(12) United States Patent
Abdel-Rahman et al.

(10) Patent No.: US 6,248,158 B1
(45) Date of Patent: Jun. 19, 2001

(54) OVEN HOUSING MODULE IN AN ANALYTICAL INSTRUMENT

(75) Inventors: Mahmoud F. Abdel-Rahman, West Grove; Roger L. Firor, Landenberg, both of PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/364,453

(22) Filed: Jul. 30, 1999

(51) Int. Cl.$^7$ ............................................... B01D 15/08
(52) U.S. Cl. ............................ 96/101; 95/87; 96/102; 210/198.2
(58) Field of Search ........................ 95/87; 96/101–107; 210/198.2

(56) References Cited

U.S. PATENT DOCUMENTS

| | | | |
|---|---|---|---|
| 3,165,147 | * | 1/1965 | Roof et al. ........................ 96/102 X |
| 3,306,347 | * | 2/1967 | Favre ................................... 95/87 |
| 3,422,603 | * | 1/1969 | Redmond, Jr. ........................ 96/103 |
| 4,038,055 | * | 7/1977 | Varano et al. ........................ 96/102 |
| 4,050,911 | * | 9/1977 | Welsh ................................. 96/103 |
| 4,181,613 | * | 1/1980 | Welsh et al. ...................... 96/104 X |
| 4,580,036 | * | 4/1986 | Hunt et al. ........................ 96/101 X |
| 4,599,169 | * | 7/1986 | Ray .................................. 96/101 X |
| 4,771,628 | * | 9/1988 | Sisti et al. ......................... 96/101 X |
| 4,869,876 | * | 9/1989 | Arfman et al. ..................... 96/102 X |
| 5,447,556 | * | 9/1995 | Pleil et al. ............................... 95/87 |
| 5,634,961 | * | 6/1997 | Gordon .............................. 95/87 X |
| 5,656,170 | * | 8/1997 | Henderson ......................... 95/87 X |
| 5,744,029 | * | 4/1998 | Li et al. ............................. 95/87 X |
| 5,807,426 | * | 9/1998 | Ohtsuki et al. .................... 95/87 X |
| 5,830,262 | * | 11/1998 | Marchini et al. ................ 96/101 X |
| 5,830,353 | | 11/1998 | Henderson ....................... 210/198.2 |

* cited by examiner

Primary Examiner—Robert H. Spitzer

(57) ABSTRACT

Energy efficiency of a thermal zone in an analytical instrument is improved by use of an oven housing module having an enclosure body defining an oven cavity, wherein the enclosure body exhibits a size and shape sufficient to receive a component to be subjected to temperature control within a thermal zone located in the oven cavity. A temperature control assembly includes a vent assembly communicating with ambient air, a fan, and a fast cooling flap, wherein the temperature of the thermal zone may be modulated by supplementing the oven cavity air with ambient air. The fast cooling flap may be operated for opening one side of the oven cavity to ambient conditions such that ambient air may be rapidly introduced to the oven cavity and the cavity air may be rapidly exhausted from the oven cavity for rapid cooling of the thermal zone. The oven cavity is very compact so as to allow only a marginal amount of cavity volume to be disposed about the temperature-controlled component, so as to permit efficient circulation of cavity air around the component for efficient temperature control of the component, and yet minimize the volume of the oven cavity, thus reducing the effective thermal mass of the enclosure body.

20 Claims, 5 Drawing Sheets

OVEN HOUSING MODULE IN AN ANALYTICAL INSTRUMENT

FIELD OF THE INVENTION

The present invention relates to methods and apparatus for the provision of a controlled thermal environment, and, more particularly, for an oven housing module suitable for effecting thermal control of a component located therein.

BACKGROUND OF THE INVENTION

Modern analytical instruments are particularly susceptible to performance variations due to the thermal sensitivity of certain components that operate within the analytical instrument. The temperature of one or more components of an analytical instrument is typically controlled by locating the component in a temperature-controlled environment, or thermal zone. The temperature of the thermal zone is typically effected by an electrically-powered heating device or cooling device, or a combination of such devices.

One particular type of analytical instrument is a chromatograph. The basic components of a chromatograph include an injection port for introducing a sample of matter to be examined into a stream of carrier fluid, a separation column attached to the injection port that causes some of the constituents of the sample to elute at different times, and a detector for producing a signal indicative of the presence of the constituents being eluted. A signal processing section may be employed for integrating the signal so as to provide information as to the quantity of each constituent.

In the typical gas chromatograph, the temperature controlled zone is provided within an oven cavity. The injection port and detector are attached to respective pneumatic fittings on the oven housing, and the separation column, usually mounted on a basket, is attached between the pneumatic fittings and located within the oven cavity. The oven housing typically comprises a fast-cooling flap and an enclosure having several insulated oven housing walls. A heating element and a stirring fan located in the oven cavity respectively heats and stirs the air contained within the oven cavity so as to minimize temperature gradients therein that could adversely affect the performance of the chemical process occurring within the column. During a typical sample analysis, the heating element is operated so as to increase the temperature of the oven from a minimum initial value to a final value. Before introduction of the next sample into the column, the temperature of the oven is usually returned to its initial value.

The conventional chromatograph is typically constructed for operation of one or more capillary columns that are wound on 5 inch (or larger) diameter baskets. Additional components may also be designed for operation within the thermal zone. A large oven cavity (typically over one thousand cubic inches) is often built to accommodate the foregoing requirements. The typical oven cavity housing is constructed of an inner wall of thin stainless-steel surrounded by some type of soft insulation, which in turn is surrounded by an outer casing of structural sheet metal.

High resolution gas chromatography requires that the oven temperature be varied from an initial temperature to a final temperature, according to a precisely controlled profile, as known in the art. After the oven reaches its final temperature, the analysis is considered to be complete. However, to begin a new analysis, the oven must be cooled to a predetermined initial temperature. Cooling is typically accomplished by opening a vent in the rear of the oven cavity. This method of cooling is inefficient and usually results in a long cooling cycle due to the recirculation of considerable amounts of heated air.

The entire oven cavity is subject to these repeated patterns of heating and cooling. Accordingly, with repeated cycling of the heating unit, fan, and other such devices, a large amount of energy is generated and dissipated, and thus the chromatograph consumes a considerable amount of power.

In some applications, the temperature control system may be expected to produce an especially fast oven temperature ramp rate. However, such a rate causes the temperature control system to consume an even greater amount of electrical current, one which is beyond the amperage typically available from a single mains socket (e.g., over 15 amps). Oven designs that are capable of programmed temperature ramp rates beyond 60 degrees centigrade per minute will therefore require a voltage supply that exceeds 120 volts AC.

Furthermore, the time required for heating and cooling the oven cavity is too long. The time required to cool the oven will reduce the throughput of the instrument and the overall efficiency of the oven is not optimal.

Accordingly, the conventional chromatograph is best suited for use in the laboratory, or similar settings, where sufficient space and electrical power are available. There have been attempts to reduce the size and complexity of a chromatograph so as to be practical outside of the laboratory. Such miniaturization has not been fully realized, due in part to the power demands put on the system by an inefficient oven, and due to the large size and large thermal mass that is presented by the typical oven housing.

There is accordingly an unresolved need for a more compact, reliable, and energy efficient system for providing the requisite control of a thermal zone, so as to effect,inter alia, faster analysis, in an analytical instrument.

SUMMARY OF THE INVENTION

We have determined that the energy efficiency of a thermal zone in an analytical instrument is improved by use of a compact oven cavity in an oven housing module wherein a fan and a fast cooling flap are provided, wherein the fast cooling flap may be operated for opening at least one side of the oven cavity to ambient conditions, such that heated cavity air may be rapidly exhausted from the oven cavity.

In a preferred embodiment, the oven module features an enclosure body formed of rigid insulating material that encloses the oven cavity in which is the desired thermal zone. This novel oven housing module has less thermal mass and accordingly retains less heat than the conventional oven housing, so as to reduce not only the the amount of heating or cooling required for temperature control of a component positioned therein, but also the time required for effecting thermal changes, thus accomplishing a much faster analysis.

The thermal response of the oven module, that is, the time necessary for adjusting the temperature of the thermal zone by a temperature control assembly is greatly improved. Accordingly, temperature changes according to an oven temperature profile (e.g., ramp rate) may be accomplished faster and more efficiently than found in the prior art.

In a particularly preferred embodiment of the invention, the oven housing module includes, in the enclosure body, a fast-cooling flap constructed of rigid insulating material, wherein the enclosure body exhibits a size and shape sufficient to enclose the oven cavity and define therein a thermal zone, whereby the oven housing module impedes heat transfer between the thermal zone and ambient conditions. The body includes an interior surface which faces the thermal zone. The oven housing module includes an oven vent assembly and an oven fan assembly having a fan. The oven cavity in the enclosure body is shaped so as to provide a thermal envelope about the component, whereby the envelope corresponds to the volume occupied by the component located in the thermal zone and includes a marginal volume disposed about the component so as to permit a primary air flow to be directed by the fan around the component for efficient temperature control of the component.

In one aspect of the invention, the fast cooling flap, adjustment of the fast-cooling flap position alters the primary air flow about the component so as to draw a secondary flow of ambient air rapidly across the oven walls and through the volume occupied by the component, and then directed out of the oven cavity, whereby such efficient circulation of the primary air flow through the thermal zone effects very rapid cooling of the component, the cavity air, and the wallsof the oven cavity.

In another aspect of the invention, the oven housing module includes a temperature control assembly wherein portion of the enclosure body is shaped to include an air duct that communicates between the ambient conditions and the oven cavity, whereby a secondary (i.e., ambient) air flow through the duct may be selectably directed to complement the primary air flow between the perimeter of the first space from the central portion of the oven cavity. Hence, ambient air may be used to modulate the temperature of the thermal zone in the oven cavity In another aspect of the invention, the component is preferably provided in the form of a coiled separation column locatable at a central portion of the oven cavity, and wherein the coiled separation column is preferably integrated into a module also having an inlet and a detector to provide a removable assembly which may be inserted into a port in the housing, such that the coiled separation column is positioned between the perimeter of the oven cavity and the central portion of the oven cavity.

The advantages of the invention may also be realized in a preferred embodiment of a chromatograph suitable for use with a control system so as to provide an analytical instrument. The chromatograph includes a housing having an enclosure body formed of rigid insulating material shaped for defining an oven cavity therein; a temperature control assembly for establishing a thermal zone in the oven cavity; an injector section, a detector section, and a separation column locatable within the thermal zone and having inlet and outlet ends attached to the injector section and detector section; and a fast-cooling flap mounted on a fast-cooling flap opening in the enclosure body which allows rapid movement of cavity air from the thermal zone. The enclosure body exhibits a compact size and shape sufficient to accommodate a compact separation column within the thermal zone and to thermally isolate the thermal zone from ambient conditions. In the preferred embodiment, the oven cavity occupies less than 90 cubic inches.

The chromatograph includes an oven vent assembly that includes a duct which communicates between the ambient conditions and the oven cavity, whereby ambient air flow through the duct may be selectably directed to complement the primary air flow between the perimeter of the first space from the central portion of the first space.

The oven housing module includes a fast-cooling flap, whereby the movement of the fast-cooling flap is configured so as to allow rapid air flow from the thermal zone to ambient conditions when the fast-cooling flap is opened.

The oven housing module optionally includes modular housing subsections each of which are composed of rigid insulating material, wherein a plurality of subsections may be assembled to provide the enclosure body.

The injector section, detector section, and separation column are preferably provided in a modular assembly locatable on a top loading port in the oven housing module, whereby the separation column is locatable in the thermal zone while its inlet and outlet ends remain attached to the injector section and detector section, such that the modular assembly may be positioned in a first position wherein the separation column is positioned in the oven cavity, and then at least one of the injector section, detector section, and separation column may be retracted from the first position to a second position outside of the oven housing module to accommodate repair or replacement of the injector section, detector section, or separation column.

Use of the rigid insulating material as the basic structure for the enclosure body allows significant reduction in the thermal mass of the oven housing module, and allows the dimensions of the oven cavity to be reduced so as to provide a thermal zone optimally configured according to the dimensions of the separation column. The thermal zone, being smaller, may be heated more efficiently and thus the temperature control assembly consumes less operating power in comparison to oven is constructed according to the prior art. As an added benefit, unimpeded access to the oven cavity is maintained and the tasks of mounting or replacing a separation column are easily done.

BRIEF DESCRIPTION OF THE DRAWINGS

The present invention will be better understood, and its numerous objects and advantages will become apparent by reference to the following detailed description of the invention when taken in conjunction with the following drawings, in which.

DETAILED DESCRIPTION OF THE PREFERRED EMBODIMENTS

Figure 1:
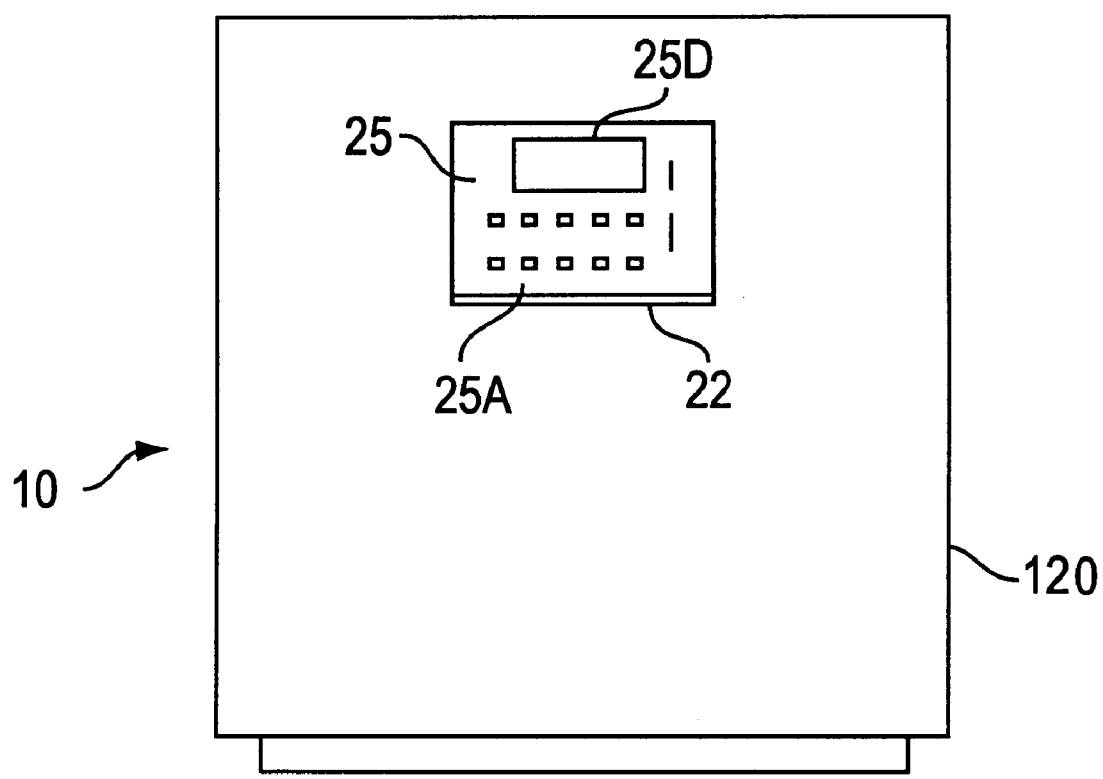
FIG. 1 is a front perspective view of a novel analytical instrument configured as a chromatograph and constructed in accordance with the present invention.

The present invention will find useful application in a variety of analytical systems that benefit from thermal control of a component positioned in a thermal zone in the analytical instrument.

The analytical instrument of the present invention may be employed in particular to provide separation with respect to one or more of such fluid streams. Gases are the preferred fluids according to the practice of the present invention, and therefore the following description of the invention will include a description of the arrangement, construction, and operation of oven housing module suitable for use in an analysis of a gaseous stream in a gas chromatographic analytical system (hereinafter, a chromatography. However, for the purposes of the following description, the term "fluid" will also be considered to refer to all types of fluids.

It should be understood that the teachings herein are applicable to other analytical instruments, including liquid chromatographs, high-pressure gas chromatographs (HPGC), combined chromatographic and mass spectrometry systems (GC/MS), supercritical fluid chromatographs (SFC), and supercritical fluid extraction (SFE) instruments.

In one aspect of the present invention, the apparatus and methods of the present invention are directed to the provision of selective temperature control of a component situated in a temperature-controlled thermal zone in an analytical instrument. However the teachings of the present invention may also be applied to any analytical instrument that may benefit from the provision of a controlled temperature in a closed cavity.

The present invention is contemplated for use in a compact and efficient analytical instrument that will find advantageous use not only in a laboratory but also outside of the laboratory. The teachings of the present invention may therefore be applied to both portable and laboratory-based analytical instruments, as well as to other types of portable instruments that may benefit from the provision of a temperature controlled thermal zone or a selectable cavity volume.

"Thermal zone" is meant to describe a temperature-controlled volume of air within which a component is positioned and thereby subject to the air temperature in the thermal zone. In effect, the function of the thermal zone is to control the temperature of the component by way of a temperature-controlled air bath.

"Component" and "module" are meant to include one or more devices, subsystems, or assemblies that may form a portion of an analytical instrument. In the illustrated embodiments, a separation column may be mounted as a component in an oven module which is operable in a gas chromatograph. However, the teachings of the present invention may be applied to the construction of an oven module for temperature control of other components as well.

"Analysis" and "analytical" are meant broadly to include both qualitative and quantitative analytical methods, detection, or observation of physical or chemical parameters. For example, the apparatus and methods described herein may be applied to directly or indirectly effect selective temperature control of an element, substance, or material in the form of a "sample" that is present in, or processed by, such analysis.

"Chromatographic" analysis of a sample is the preferred mode of analysis according to the practice of the present invention, and the following description of the invention will be directed to an analytical instrument in the form of a compact gas chromatographic analytical system (hereinafter, a chromatograph). However, the teachings herein may be applied to analytical instruments for effecting a chromatographic analysis of liquids, multiple component gases and liquids, and mixtures thereof capable of flow. Moreover, it should be understood that the teachings herein are applicable to instruments that operate using other instrument methods or that analyze or detect other physical parameters and phenomena. Sample extraction or sample trapping are but two such methods that represent alternative applications.

In the Figures and in the description to follow, like nomenclature and numeric identifiers will refer to like components; virtual or imaginary components such as air flow vectors are schematically drawn in bold lines; and insulating material is illustrated in cross-hatched lines.

Figure 2:
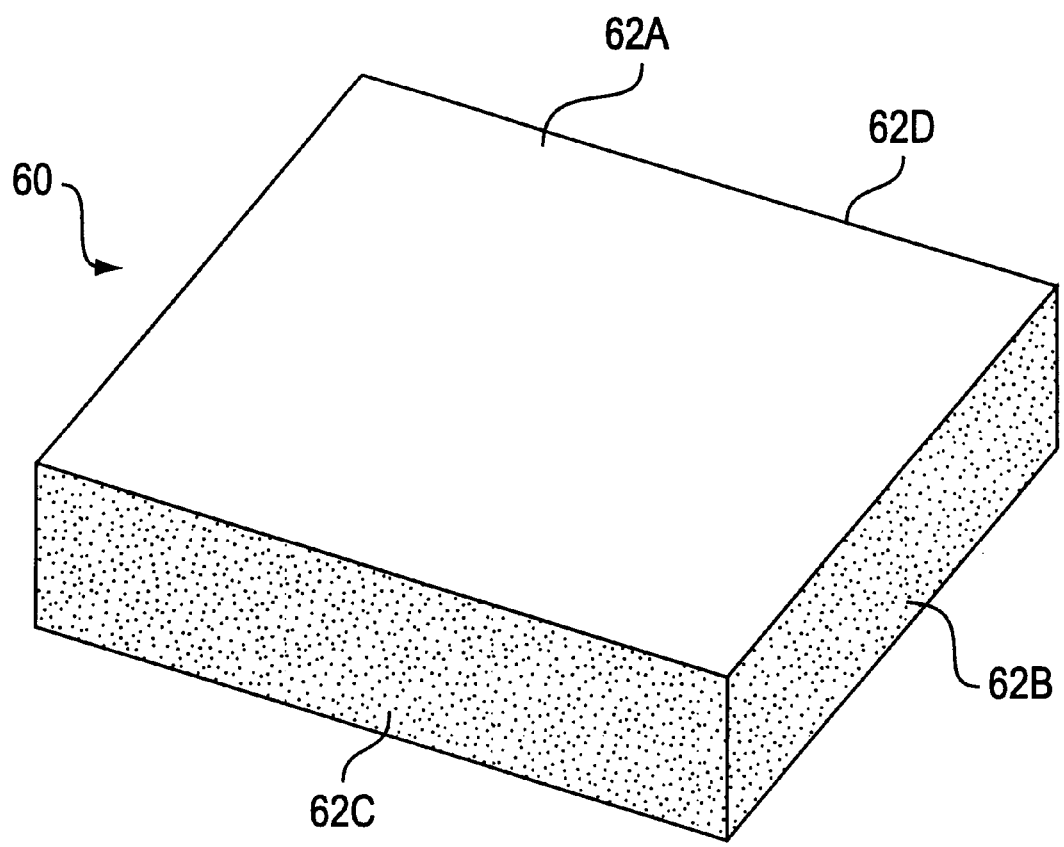
FIG. 2 is a side perspective view of a preferred embodiment of a section of rigid insulating material constructed in accordance with the present invention for use in a oven housing module operable in the chromatograph of FIG. 1.
Figure 3:
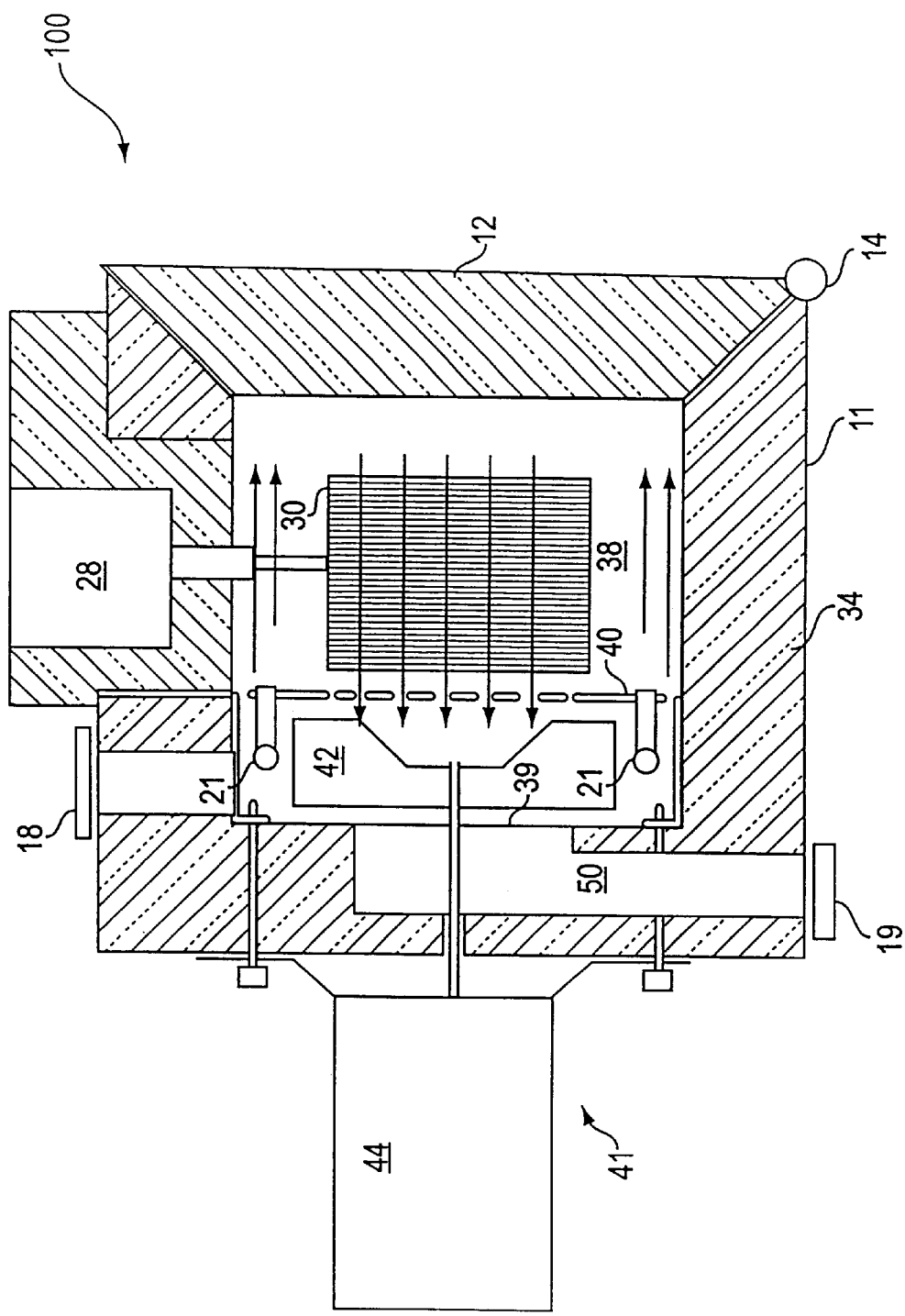
FIG. 3 is a side sectional view of a preferred embodiment of an oven housing module operable in the chromatograph of FIG. 1, illustrating a first active operating condition, wherein a single separation column is installed in the oven cavity and the fast-cooling flap is closed during heating of the oven cavity.
Figure 4:
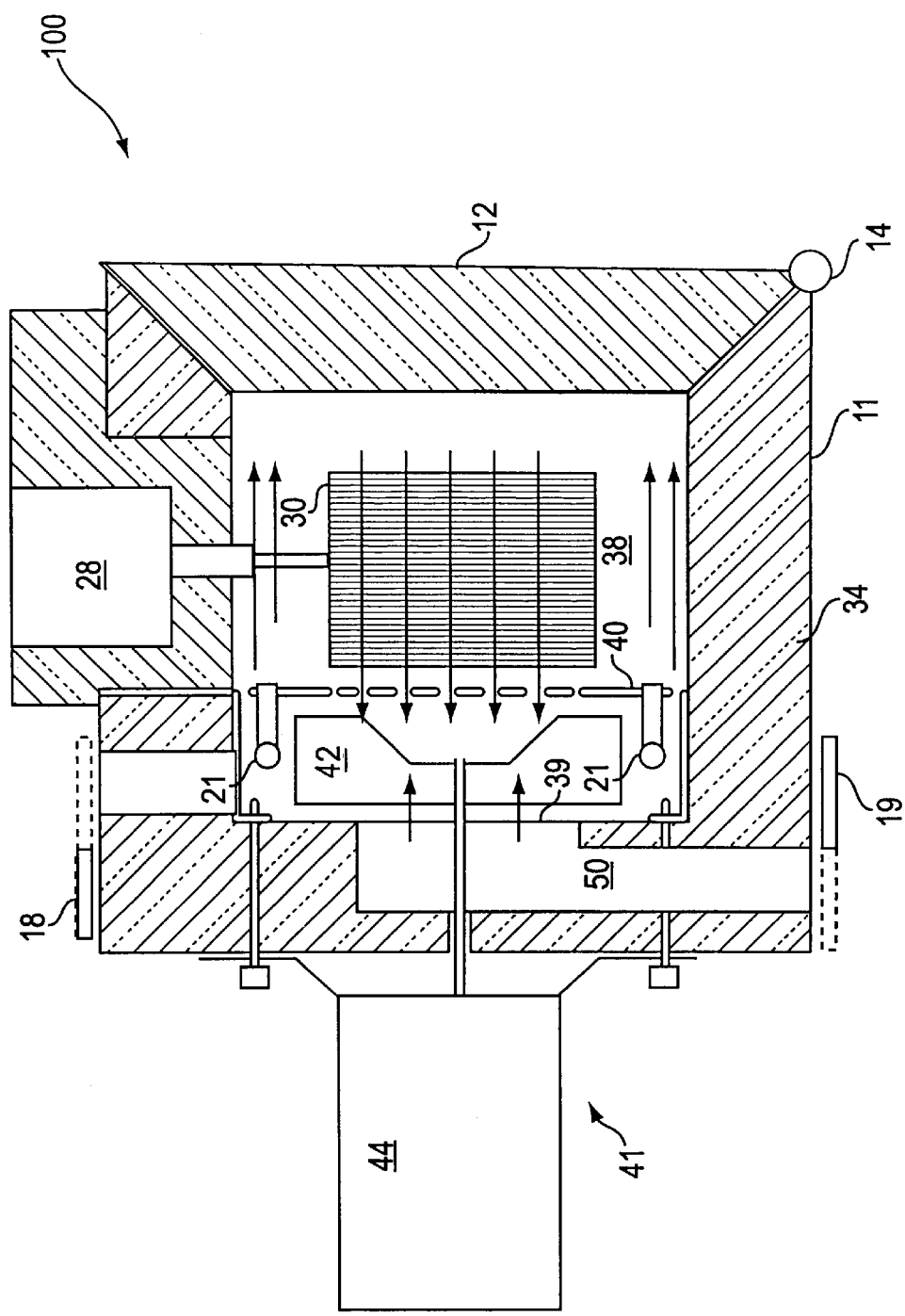
FIG. 4 is a side sectional view of the module of FIG. 3 during a second active operating condition, wherein the temperature of the thermal zone is modulated with ambient air.
Figure 5:
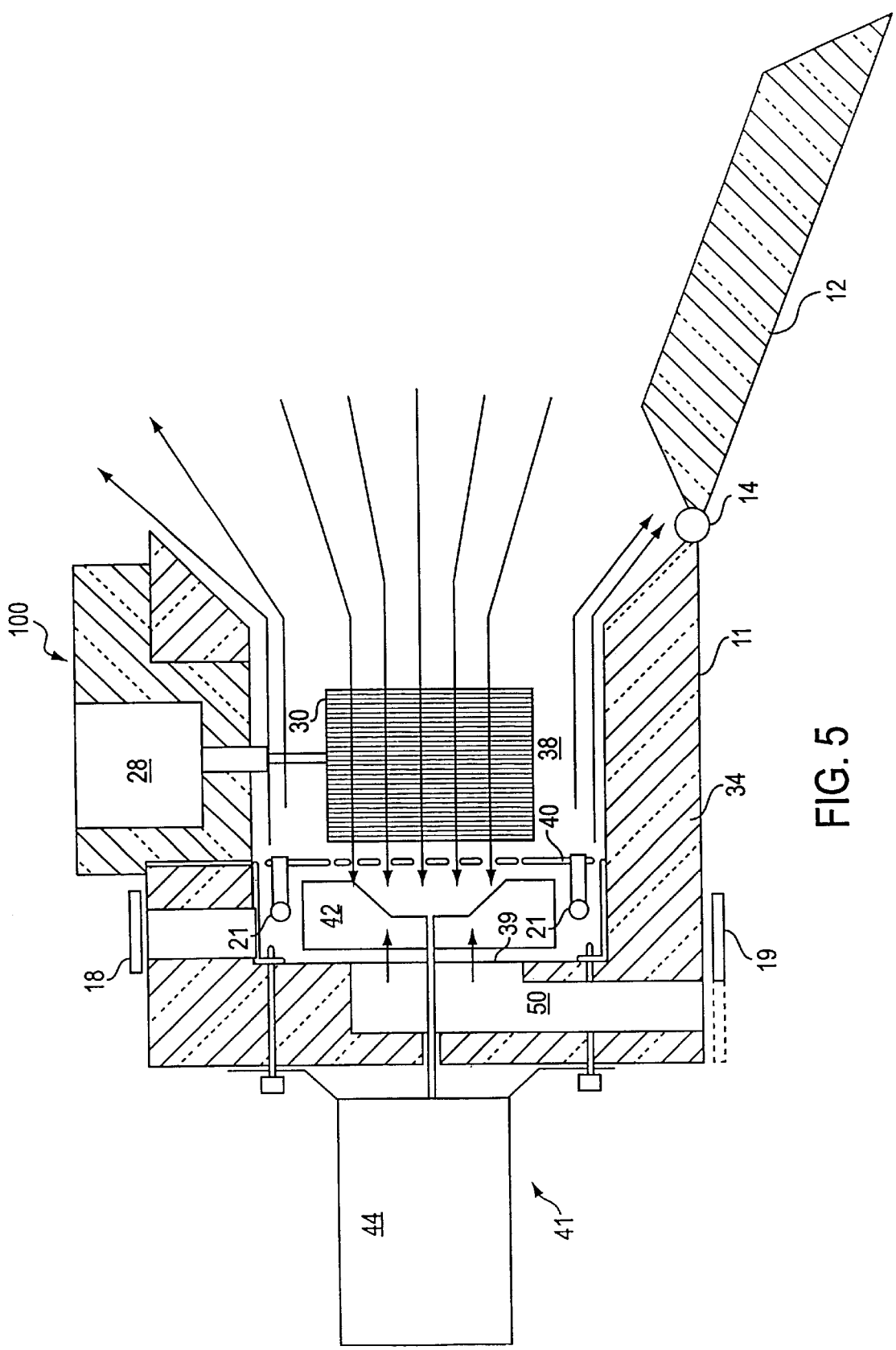
FIG. 5 is a side sectional view of the module of FIG. 3 during a third active operating condition, wherein the fast-cooling flap is opened for rapid cooling of the oven cavity.

A first preferred embodiment of a new and novel gas chromatograph is shown in FIG. 1 and is generally designated 10; an oven housing module operable in the chromatograph of FIG. 1 is illustrated in FIGS. 3–5 and is generally designated 100; a preferred embodiment of a section of rigid insulating material suitable for construction of an enclosure body in the oven module 100 of FIGS. 3–5 is shown in FIG. 2 and is generally designated 60.

As shown in FIG. 1, the chromatograph 10 is arranged to perform a chromatographic separation of a given sample compound in an analysis. The illustrated embodiment utilizes a sample injection with a pressurized carrier gas by means of an injection port in a modular inlet and detector assembly 28. The carrier gas supplied to injection port is provided from a source through an appropriate valve (not shown), which serves to control the pressure of the carrier gas flowing in a column 30 connected to the assembly 28. However, for the purposes of this description, the sample may be considered as being injected using any conventional technique.

The chromatograph 10 includes a chromatograph housing 120 within which the oven housing module 100 is contained. The separation column 30 is positioned within the oven housing module 100 having an oven cavity 38, and a temperature control assembly which provides heat or cooling to a thermal zone in the oven cavity 38 in response to a control signal generated by computer 22, in order to ensure that the temperature within the oven housing module 100 is at a desired level, as known in the art. The carrier gas/sample combination passing through column 30 is exposed to a temperature profile resulting in part from the operation of the temperature control assembly within the oven housing module 100. During this profile of changing temperatures, i.e., rising or falling, the sample will separate into its components primarily due to differences in the volatility characteristics of each component at a given temperature. As the components exit column 30 they are detected by the detector in the assembly 28.

Oven housing module 100 has a generally cubic shaped cavity 38 defined by an enclosure body 34 formed of rigid insulating material, a sample of which is illustrated in FIG. 2 as a subsection 60 having a working surface 62A and sides 62B, 62C, 62D.The illustrated embodiment of the enclosure body 34 includes modular sections of rigid insulating material in various configurations that are shaped according to the requisite design of the oven cavity 38. A fast-cooling flap 12 preferably is mounted on a flap actuator 14 located at the base 11 of the enclosure 34 and is selectably movable between a fully open position (illustrated in FIG. 5, which provides complete access to the oven cavity 38) and a closed position (illustrated in FIG. 1, which completely closes off and contains oven cavity 38). The construction of the fast-cooling flap 12 may differ according to the application; alternative embodiments of the fast-cooling flap may include one or more segmented, iris-type, or sliding panels, and so on.

The temperature control assembly includes: ambient air flaps 18,19 and the fast cooling flap 12 (each of which are selectably positionable according to conventional means, not shown), a heater 21, and an oven vent assembly 50. Ambient air may be supplied to the oven cavity 38 by way of a duct in the oven vent assembly 50. An oven fan assembly 41 includes an oven fan 42 and motor 44, the combination of which can be located at any interior wall of the enclosure 34, but as shown the oven fan assembly 41 is located opposite the fast-cooling flap 12 and thus at the rear wall 39. The duct in the oven vent 50 includes exhaust and intake ports respectively located at flaps 18,19, and is preferably provided as an airway that communicates to the oven cavity 38 through the rear wall 39. Airflow (illustrated by bold arrows) in the oven cavity 38 may be selectably controlled by the operation of the temperature control assembly and by the oven fan assembly 41 according to rotation of the fan 42 by motor 44.

In a particular feature of the present invention, the fast-cooling flap 12 may be opened to allow rapid cooling of the oven cavity 38. Otherwise, when the intake and exhaust ports are covered, and when the fast-cooling flap 12 is closed, the oven 16 defines a substantially closed, thermally-insulated volume of air which may be considered as the enclosed cavity air during such conditions.

Mounted in the oven cavity 38 behind the space containing the column 30 is a transverse baffle 40 of sheet metal having a central opening covered by a protective grid. Baffle 40 is connected at its periphery to the interior side walls of the enclosure 34. The dimensions of baffle 40 are less than that of the corresponding dimensions of cavity 38 to provide a peripheral space permitting air to flow from a central portion of the oven cavity to the rear of the oven cavity 38 and then towards the front of the oven cavity as shown by the bold arrows. The fan 42 is mounted behind baffle 40 and is surrounded by a portion of a marginal volume of the oven cavity 38 which also surrounds the separation column 30. Fan 42 is driven by motor 44. The oven fan 42 is mounted on a shaft extending through the rear wall 39 and is rotatable by known techniques in a selected direction. In certain operating conditions, temperature sensors (not shown) located priximate to the column 30 sense the temperature of the air bath as the fan 42 circulates air across the heater 21 within the oven cavity 38 in a controlled manner so as to thermostatically establish the temperature of a thermal zone.

The baffle 40 in the oven defines a circular central opening about the oven fan 42.

The baffle 40 is spaced from the inner side walls by tabs so as to provide a structure having a matrix of openings through which cavity airflow may occur in a stirring flow. Preferably, the heater 21 is mounted on a loop located proximate the outermost tips of the blades of the fan 42 and separated therefrom by a gap of approximately 0.125 inches. As indicated by the bold arrows that represent air flow direction, cavity air is normally taken from the front of the baffle through the central opening and is thrown outwardly by the fan 42 over the heater 21, and then forwardly into the front portion of cavity 38. Thus the stirring flow of air in the oven cavity is preferably effected in the form of a vortex. The baffle 40 creates turbulence and provides air mixing to insure a uniform temperature within the thermal zone. The temperature control assembly may be operated to allow oven fan 42 to be rotated in a direction by motor 44 so as to move temperature-controlled air (or ambient air, when necessary) through the assembly to the oven cavity 38. The operation of the temperature control assembly is used to regulate the desired temperature within the oven 16. Note that the heater 21 into temperature control assembly may alternatively include one or more resistive wire units, a cryogenic device, or may be provided in the form of a thermoelectric heating and cooling device such as a Peltier device, or as a combined resistive heating and cryogenic cooling device.

Computer 22 maintains overall control of a plurality of functions associated with the operation of the gas chromatograph 10. For example, the computer 22 provides coordinated control of the temperature control assembly, the oven vent assembly 50, and the oven fan assembly 41. One or more of the temperature sensors (not shown) sense the air bath temperature in the oven cavity 38 and transmit a feedback signal representative of such temperature to computer 22. Computer 22 may thereby regulate the flow of ambient air into the oven cavity 38, and the flow of cavity air about the separation column 30 to establish the desired temperature in the separation column 30. Although computer 22 is shown as a single block, such computer preferably includes one or more printed circuit board assemblies and includes a central processing unit and all associated peripheral devices, such as random access memories, read-only memories, input/output isolation devices, clocks, drivers, power supply, interface circuits, and other related electronic components. As such, computer 22 includes a memory in which information and programming, directed to a plurality of control functions can be stored and retrieved by known methods.

Accordingly, the chromatograph 10 includes a control panel 25 connected to computer 22. The control panel 25 includes data entry devices such as keypad 25A for entry of various pieces of information into computer 22 by the user, and computer 22 operates to act upon the entered information or to store the entered information into memory for later access. Control panel 25 is provided with a display screen 25D. Consequently, indicating or prompt messages, such as may be pertinent to a shutdown or an inactive mode, can be generated by computer 22 and displayed on the display screen 25D.

The preferred embodiment of the chromatograph 10 in FIG. 1 is illustrated as a top-loading chromatograph, although the description herein is generally applicable to other embodiments.

In a particular feature of the invention, it is contemplated that any unused space created within the thermal zone in the oven cavity 38 will waste energy; further, as the volume of the oven cavity is reduced, less power is required to heat or cool the oven cavity and the efficiency of the temperature control assembly is increased. Furthermore, as the volume of the oven cavity is reduced, the thermal mass presented by the oven housing module 100 to the temperature control assembly can be reduced as well. Additionally, the preferred close proximity of the blade tips of the fan 42 to the heater 21 allows the heater 21 to be operated at a higher power then allowed in conventional oven heater designs and also improves the thermal response of the oven because the thermal delay of heat transfer from the heater 21 to the oven cavity 38 is reduced. For example, preferred embodiments utilizing a resistive heater have been constructed according to the teachings herein to accomplish oven ramp rates of up to 600 degrees centigrade per minute with use of a resistive heater which draws a current level within a maximum of 15 amps.

Preferably, the enclosure body 34 is composed of a rigid insulating material. A suitable embodiment of a subsection 60 of the enclosure body 34 is shown in FIG. 2. Such material may be used to construct the entire enclosure body 34 according to the requisite dimensions of the oven cavity 38, and may be used to form movable components such as fast-cooling flap 12, so as to provide a rigid, compact structure that is shaped to occupy as much of the unused space in the oven cavity 38 as possible without obstructing the circulation of air in the air bath described above with respect to the column 30. The rigid insulating material in enclosure body 34 is composed preferably of material that not only impedes heat transfer between the thermal zone and ambient conditions, but also is functional as a rigid substrate upon which components such as the fan assembly 41 may be mounted, and in which passageways, such as the duct in the oven vent assembly 50, may be provided. Preferred high-temperature (e.g., refractory) rigid insulating materials include calcium silicate insulating board, which is available commercially in the form of "Super Firetemp" from the Mesa Insulation division of Johns-Manville, Fruita, Colo., USA. A protective "skin" may be incorporated in one or more of the exposed working surfaces 62A so as to protect the enclosure body 34 from the effects of handling or impact.

Preferred embodiments of the enclosure body 34 may be molded, extruded, etc., or formed by assembly of subsections using adhesives or similar methods, so as to provide a complete, rigid enclosure body 34 upon which components such as the fast-cooling flap 12 are easily mounted. The oven housing module 100 may therefore be constructed to provide a selectable volume for the oven cavity 38.

Hence, the enclosure body 34 is easily manufactured using either: a) an aggregation of prefabricated subsections, such as subsection 60, of which the number, size, and shape may be selected and quickly assembled to create a desired oven cavity, so as to best fit the component to be subjected to temperature control, and to thereby conform to irregularities in the component located in the oven cavity; or b) a single mass of rigid insulation material having a predetermined configuration obtained during extrusion, molding, etc.

Preferred embodiments of the enclosure body 34 are formed so as to enclose the oven cavity 38 and isolate therein a thermal zone from ambient conditions, whereby a component such as the column 30 (and optionally other components) may be located within the thermal zone, and wherein heat transfer is impeded between the thermal zone and ambient conditions by the rigid insulating material. Hence, and depending upon the application, the shape and configuration of the oven housing module 100 may be precisely defined to accommodate the irregular dimensions of the component(s) to be located in the thermal zone; further, the enclosure body 34 advantageously includes interior and exterior surfaces that are sufficiently rigid so as serve as a substrate upon which a variety of components, such as the oven fan assembly 41, may be mounted. Futhermore, the oven housing module 100 is readily modified to include more than one oven cavity, thus being especially useful in effecting temperature control of multiple columns individually positioned in respective oven cavities, for performing, e.g., multi-dimensional chromatography.

As particularly illustrated in FIGS. 3–5, the interior surface of the oven housing module 100 is preferably shaped so as to allow only a marginal amount of cavity volume to be disposed about the column 30, so as to permit efficient circulation of cavity air around the column 30 for efficient temperature control of the column 30, and yet substantially minimize the volume of the oven cavity 38. The compact size of the oven cavity and it's very low thermal mass allows the opening of the fast cooling flap 12 to rapidly exhaust heated cavity air without presenting a severe safety hazard. Nonetheless, preferred embodiments of the chromatograph 10 locate the majority of the oven housing module 100 within the chromatograph housing 120 such that the chromatograph housing 120 preferably includes a perforated shroud (not shown) slightly beyond of the swing radius of the fast cooling flap 12 to facilitate transfer of oven cavity air to ambient conditions and to ensure safe operation.

While the invention has been described and illustrated with reference to specific embodiments, those skilled in the art will recognize that modification and variations may be made without departing from the principles of the invention as described herein above and set forth in the following claims.

What is claimed is:

1. An oven housing module having an oven cavity therein for use in temperature control of a component situated in the oven cavity, comprising:

an enclosure body, defining the oven cavity, having a size and shape sufficient to receive the component, the enclosure body being formed of insulating material and having at least one vent and a fast cooling flap adapted to expose the oven cavity to a greater volume of air than the at least one vent, wherein the component is mounted on the enclosure body, and wherein the enclosure body is constructed to impede heat transfer between a thermal zone surrounding the component and ambient conditions; and a temperature control assembly having: a vent assembly that opens and closes the at least one vent permitting communication of the oven cavity with ambient air, a fan associated with the vent assembly, and an actuation mechanism coupled with the fast cooling flap so as to open and close the fast cooling flap, wherein the temperature of the thermal zone may be modulated by supplementing the oven cavity air with ambient air using the vent assemble and based on a Predetermined condition using the actuation mechanism such that ambient air is rapidly introduced to the oven cavity and the cavity air is rapidly exhausted from the oven cavity for rapid cooling of the thermal zone.

2. The oven housing module of claim 1, wherein the insulating material further comprises a rigid insulating material.

3. The oven housing module of claim 2, wherein the rigid insulating material further comprises calcium silicate.

4. The oven housing module of claim 1, wherein the oven cavity is shaped so as to correspond to the volume occupied by the component located in the thermal zone plus a marginal volume disposed about the component so as to permit air flow around the component for efficient temperature control of the component.

5. The oven housing module of claim 1, wherein the component is provided in the form of a separation column located in a central portion of the oven cavity, and wherein the oven cavity is shaped to permit air flow about the separation column between the perimeter of the oven cavity and the central portion of the oven cavity.

6. The oven housing module of claim 5, wherein the separation column is provided in a removable module and wherein the enclosure body includes a port for positioning at least a portion of the removable module in the oven cavity.

7. The oven housing module of claim 6, wherein the removable module includes an inlet and a detector respectively attached to inlet and outlet end of the separation column.

8. The oven housing module of claim 1, wherein the temperature control assembly includes a heater mounted adjacent the fan for controlling the temperature of the thermal zone in the oven cavity.

9. The oven housing module of claim 8, wherein the oven cavity has a total internal volume of less than 90 cubic inches.

10. A chromatograph, comprising:

an injector section, a detector section, and a separation column having inlet and outlet ends respectively attached to the injector section and detector section;

an oven housing module having an enclosure body, having a size and shape sufficient to receive the separation column, for use in temperature control of a thermal zone situated in the oven cavity and surrounding the separation column, the enclosure body defining an oven cavity, the enclosure body having at least one vent and a fast cooling flap adapted to expose the oven cavity to a greater volume of air than the at least one vent, wherein the enclosure body is constructed to impede heat transfer between the thermal zone and ambient conditions; and a temperature control assembly attached to the oven housing module for effecting temperature control of the thermal zone in the oven cavity, having: a vent assembly that opens and closes the at least one vent permitting communication of the oven cavity with ambient air, a fan associated with the vent assembly, and an actuation mechanism coupled with the fast cooling flap so as to open and close the fast cooling flap, wherein the temperature of the thermal zone may be modulated by supplementing the oven cavity air with ambient air using the vent assemble and based on a predetermined condition using the actuation mechanism such that ambient air is rapidly introduced to the oven cavity and the cavity air is rapidly exhausted from the oven cavity for rapid cooling of the thermal zone.

11. The chromatograph of claim 10, wherein the enclosure body further comprises a rigid insulating material.

12. The chromatograph of claim 11, wherein the enclosure body further comprises a port and wherein the injector section, detector section, and separation column are provided in a removable modular assembly locatable in the port, whereby the separation column is locatable in the thermal zone while its inlet and outlet ends remain attached to the injector section and detector section, and whereby the modular assembly may be positioned in a first position wherein the separation column is located in the oven cavity and wherein at least one of the injector section, the detector section, and the separation column may be removed from the first position to a second position outside of the oven cavity.

13. The chromatograph of claim 11, wherein the rigid insulating material further comprises calcium silicate.

14. The chromatograph of claim 10, wherein the enclosure body further comprises a plurality of subsections of rigid insulation material assembled to provide at least a portion of the structure of the oven housing module.

15. The chromatograph of claim 10, wherein the enclosure body further comprises a preformed mass of rigid insulation material, wherein the enclosure body provides at least a portion of the structure of the oven housing module.

16. The chromatograph of claim 10, wherein the interior of the enclosure body is shaped so as to correspond to the volume occupied by the component located in the thermal zone plus a marginal volume disposed about the separation column so as to permit air flow around the component for efficient temperature control of the separation column.

17. The chromatograph of claim 16, wherein the separation column is located in a central portion of the oven cavity, and wherein the oven cavity is shaped to permit air flow about the separation column between the perimeter of the oven cavity and the central portion of the oven cavity.

18. The chromatograph of claim 10, wherein the temperature control assembly includes a heater mounted adjacent the fan for controlling the temperature of the thermal zone in the oven cavity.

19. The chromatograph of claim 10, wherein the oven cavity has a total internal volume of less than 90 cubic inches.

20. A chromatograph comprising:

a separation column having an insertion plug formed of a rigid insulating material;

an enclosure formed of a rigid insulating material and defining a thermal zone, the enclosure forming:

a first opening for receiving the insertion plug such that the separation column can be situated in the thermal zone;

at least vent extending from the thermal zone to an outside surface of the enclosure; and a second opening having a surface area substantially larger than the at least one vents;

at least one moveable vent flap corresponding to the at least one vent, the at least one vent flap moveable between an open and closed position;

a fast cooling flap connected to the enclosure and movable from a closed position in which the second opening is closed and an open position in which the second opening is open allowing ambient air to enter therethrough;

a fan in communication with the thermal zone; and a temperature control assembly that actuates the at least one vent flap, the fast cooling flap and the fan, wherein the temperature control assembly actuates the at least one vent flap and the fan to maintain or slowly change the temperature of the temperature zone and actuates the fast cooling flap to rapidly cool the temperature zone.

* * * * *